US011759459B2

(12) United States Patent
Winston et al.

(10) Patent No.: US 11,759,459 B2
(45) Date of Patent: Sep. 19, 2023

(54) TREATMENT OF PAIN BY SUBARACHNOID ADMINISTRATION OF SUSTAINED-RELEASE LIPOSOMAL ANESTHETIC COMPOSITIONS

(71) Applicant: Pacira Pharmaceuticals, Inc., Parsippany, NJ (US)

(72) Inventors: Roy Winston, Parsippany, NJ (US); Kathy Los, Parsippany, NJ (US); Vladimir Kharitonov, Parsippany, NJ (US)

(73) Assignee: Pacira Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 17/958,780

(22) Filed: Oct. 3, 2022

(65) Prior Publication Data

US 2023/0038098 A1 Feb. 9, 2023

Related U.S. Application Data

(63) Continuation of application No. 17/790,426, filed as application No. PCT/US2021/012275 on Jan. 6, 2021.

(60) Provisional application No. 63/066,477, filed on Aug. 17, 2020, provisional application No. 63/064,760, filed on Aug. 12, 2020, provisional application No. 62/959,550, filed on Jan. 10, 2020.

(51) Int. Cl.
| | |
|---|---|
| *A61K 31/445* | (2006.01) |
| *A61P 23/00* | (2006.01) |
| *A61K 9/00* | (2006.01) |
| *A61K 9/127* | (2006.01) |
| *A61K 31/485* | (2006.01) |
| *A61P 23/02* | (2006.01) |

(52) U.S. Cl.
CPC .......... *A61K 31/445* (2013.01); *A61K 9/0019* (2013.01); *A61K 9/0085* (2013.01); *A61K 9/127* (2013.01); *A61K 31/485* (2013.01); *A61P 23/00* (2018.01); *A61P 23/02* (2018.01)

(58) Field of Classification Search
CPC .. A61K 31/445; A61K 9/0019; A61K 9/0085; A61K 31/485; A61P 23/00
See application file for complete search history.

(56) References Cited

U.S. PATENT DOCUMENTS

| | | |
|---|---|---|
| 5,316,771 A | 5/1994 | Barenholz |
| 5,817,074 A | 10/1998 | Racz |
| 8,182,835 B2 | 5/2012 | Kim et al. |
| 8,410,104 B2 | 4/2013 | Brummett |
| 8,834,921 B2 | 9/2014 | Kim et al. |
| 8,906,966 B2 | 12/2014 | Sherwood et al. |
| 8,957,779 B2 | 2/2015 | Wu et al. |
| 8,975,268 B2 | 3/2015 | Berde et al. |
| 8,975,281 B2 | 3/2015 | Berde et al. |
| 9,192,575 B2 | 11/2015 | Kim et al. |
| 9,205,052 B2 | 12/2015 | Kim et al. |
| 9,585,838 B2 | 3/2017 | Hartounian et al. |
| 10,398,648 B2 | 9/2019 | Schutt et al. |
| 2002/0039596 A1 | 4/2002 | Hartounian et al. |
| 2003/0059462 A1 | 3/2003 | Barenholz |
| 2003/0069318 A1 | 4/2003 | Dang et al. |
| 2003/0170288 A1 | 9/2003 | Carr et al. |
| 2006/0078606 A1* | 4/2006 | Kim ............... A61K 31/167 424/450 |
| 2007/0249681 A1 | 10/2007 | Sudo et al. |
| 2009/0105693 A1 | 4/2009 | Ben-David et al. |
| 2009/0202436 A1 | 8/2009 | Hobot et al. |
| 2011/0250264 A1 | 10/2011 | Schutt et al. |
| 2013/0177633 A1 | 7/2013 | Schutt et al. |
| 2013/0177634 A1 | 7/2013 | Schutt et al. |
| 2013/0177635 A1 | 7/2013 | Schutt et al. |
| 2013/0177636 A1 | 7/2013 | Schutt et al. |
| 2013/0177637 A1 | 7/2013 | Schutt et al. |
| 2013/0177638 A1 | 7/2013 | Schutt et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189349 A1 | 7/2013 | Kim et al. |
| 2013/0195965 A1 | 8/2013 | Schutt et al. |
| 2013/0306759 A1 | 11/2013 | Schutt et al. |
| 2013/0344132 A1 | 12/2013 | Kim et al. |
| 2014/0296293 A1 | 10/2014 | Andersen et al. |
| 2015/0250724 A1 | 9/2015 | Yamashita et al. |

(Continued)

FOREIGN PATENT DOCUMENTS

| | | |
|---|---|---|
| CN | 109745607 | 5/2019 |
| RU | 2307671 | * 10/2007 |

(Continued)

OTHER PUBLICATIONS

Mayfileld Clinic, Epidural Steroid Injections (ESI), Mayfield rain and Spine. (Year: 2018).*
Hadzic et al., "Liposome Bupivacaine Femoral Nerve Block for Postsurgical Analgesia after Total Knee Arthroplasty," Anesthesiology, Jun. 2016, 124(6):1372-1383.
Surdam et al., "The Use of Exparel (Liposomal Bupivacaine) to Manage Postoperative Pain in Unilateral Total Knee Arthroplasty Patients," Journal of Arthroplasty, 2015, 30:325-329.
[No Author Listed] [online], "Highlights of Prescribing Information—Exparel," accessdata.fda.gov, Apr. 2018, retrieved on Jun. 17, 2022, retrieved from URL <www.accessdata.fda.gov/drugsatfda_docs/label/2018/022496s9lbl.pdf>, 28 pages.

(Continued)

*Primary Examiner* — Carlos A Azpuru
(74) *Attorney, Agent, or Firm* — Fish & Richardson P.C.

(57) ABSTRACT

In some embodiments provided herein is a method of treating pain, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

19 Claims, No Drawings

(56) References Cited

U.S. PATENT DOCUMENTS

| | | |
|---|---|---|
| 2016/0000705 A1 | 1/2016 | McDonald et al. |
| 2016/0089335 A1 | 3/2016 | Ohri et al. |
| 2016/0361260 A1 | 12/2016 | Schutt et al. |
| 2016/0375140 A1 | 12/2016 | Ottoboni et al. |
| 2017/0007549 A1 | 1/2017 | Yum et al. |
| 2018/0092847 A1 | 4/2018 | Schutt et al. |
| 2019/0231762 A1 | 8/2019 | Verity |
| 2022/0015738 A1 | 1/2022 | Harbi et al. |
| 2022/0096116 A1 | 3/2022 | McFarland et al. |
| 2022/0273564 A1 | 5/2022 | Slonin et al. |
| 2022/0218610 A1 | 7/2022 | Sionin |
| 2022/0218613 A1 | 7/2022 | Slonin et al. |
| 2022/0387318 A1 | 12/2022 | Winston |
| 2023/0042662 A1 | 2/2023 | Los et al. |
| 2023/0052319 A1 | 2/2023 | Winston et al. |
| 2023/0087140 A1 | 3/2023 | Winston et al. |
| 2023/0130180 A1 | 4/2023 | Los et al. |

FOREIGN PATENT DOCUMENTS

| | | |
|---|---|---|
| RU | 2307675 | 10/2007 |
| WO | WO 1997/003652 | 2/1997 |
| WO | WO 1999/013865 | 3/1999 |
| WO | WO 1999/044640 | 9/1999 |
| WO | WO 2016/174661 | 11/2016 |
| WO | WO 2018/226732 | 12/2018 |
| WO | WO 2018/237109 | 12/2018 |
| WO | WO 2021/141956 | 7/2021 |
| WO | WO 2021/141959 | 7/2021 |

OTHER PUBLICATIONS

[No Author Listed] [online], "Marcaine [package insert]," accessdata.fda.gov, Oct. 2011, retrieved on Jun. 21, 2022, retrieved from URL <https://www.accessdata.fda.gov/drugsatfda_docs/label/2012/018692s015lbl.pdf>, 30 pages.

[No Author Listed] [online], "Naropin [package insert]," accessdata.fda.gov, Nov. 2018, retrieved on Jun. 21, 2022, retrieved from URL <https://www.accessdata.fda.gov/drugsatfda_docs/label/2018/020533s035lbl.pdf>, 30 pages.

Ahiskalioglu et al., "Can high volume pericapsular nerve group (PENG) block act as a lumbar plexus block?" Journal of Clinical Anesthesia, May 2020, 61:109650, 2 pages.

American Society of Anaesthesiologists Task Force on Acute Pain Management, "Practice guidelines for acute pain management in the perioperative setting: an updated report by the American Society of Anesthesiologists Task Force on Acute Pain Management," Anesthesiology, Feb. 2012, 116(2):248-273.

American Society of Anesthesiologists, "ASA Physical Status Classification System," asahq.org, Dec. 13, 2020, retrieved from URL <https://www.asahq.org/standards-and-guidelines/asa-physical-status-classification-system>, 4 pages.

Beachler et al. "Liposomal bupivacaine in total hip arthroplasty: Do the results justify the cost?" Journal of Orthopaedics, 2017, 14:161-165.

Bigeleisen et al., "Novel approaches in pain management in cardiac surgery," Curr Opin Anaesthesiol. Feb. 2015, 28(1):89-94.

Bronson et al. "Unanticipated transient sciatic nerve deficits from intra-wound liposomal bupivacaine injection during total hip arthroplasty," Arthroplasty Today, 2015, 1:21-24.

Chughtai et al., "Liposomal Bupivacaine Is Both Safe and Effective in Controlling Postoperative Pain After Spinal Surgery in Children: A Controlled Cohort Study," Clin Spine Surg., 2020, 33(10):E533-E538.

Cohen et al., "Incidence of adverse events attributable to bupivacaine liposome injectable suspension or plain bupivacaine for postoperative pain in pediatric surgical patients: A retrospective matched cohort analysis," Paediatr Anaesth., 2019, 29(2):169-174, 15 pages.

Day et al., "Extended Release Liposomal Bupivacaine Injection (Exparel) for Early Postoperative Pain Control Following Pharyngoplasty," J Craniofac Surg., Jul. 2018, 29(3):726-730, 4 pages.

De Leeuw et al., "The Psoas Compartment Block for Hip Surgery: The Past, Present, and Future," Anesthesiology Research and Practice, 2011, Article ID 159541, pp. 1-6.

Ecoffey, "Refresher course: Local anesthetic pharmacology in children," Regional Anesthesia and Pain Medicine, 2015, 40(5):e23-e25.

Gan, "Poorly controlled postoperative pain: prevalence, consequences, and prevention," J Pain Res. 2017, 10:2287-2298.

Gerbershagen et al., "Pain intensity on the first day after surgery: a prospective cohort study comparing 179 surgical procedures," Anesthesiology, Apr. 2013, 118(4):934-944.

Giron Arango et al., "Reply to Dr Yu et al: Inadvertent quadriceps weakness following the pericapsular nerve group (PENG) block," Reg Anesth Pain Med, May 2019, 44(5):613-614.

Gottschalk et al., "Quality of postoperative pain using an intraoperatively placed epidural catheter after major lumbar spinal surgery," Anesthesiology, Jul. 2004, 101(1):175-180.

Hu et al., "Pharmacokinetic profile of liposome bupivacaine injection following a single administration at the surgical site," Clin Drug Investig., 2013, 33(2):109-115.

International Search Report and Written Opinion in International Appln. No. PCT/US2022/011828, dated Apr. 1, 2022, 18 pages.

International Search Report and Written Opinion in International Appln. No. PCT/US2022/020713, dated Jun. 14, 2022, 24 pages.

Li et al., "Acute postoperative opioid consumption trajectories and long-term outcomes in pediatric patients after spine surgery," J Pain Res., 2019, 12:1673-1684.

Manna et al., "Probing the mechanism of bupivacaine drug release from multivesicular liposomes," J Control Release, Jan. 28, 2019, 294:279-287, 41 pages.

Mannion et al., "In with the New, Out with the Old? Comparison of Two Approaches for Psoas Compartment Block," Anesthesia and Analgesia, 2005, 101:259-264.

Mannion, "Psoas Compartment Block," Continuing Education in Anesthesia, Critical Care & Pain, 2007, 7(5):162-166.

Mazoit et al., "Pharmacokinetics of bupivacaine following caudal anesthesia in infants," Anesthesiology, Mar. 1, 1988, 68(3):387-391.

McGraw-Tatum et al. "A Prospective, Randomized Trial Comparing Liposomal Bupivacaine vs Fascia Iliaca Compartment Block for Postoperative Pain Control in Total Hip Arthroplasty," The Journal of Arthroplasty, 2017, 32:2181-2185.

Oda, "Pharmacokinetics and systemic toxicity of local anesthetics in children," Journal of anesthesia, Jun. 16, 2016, 30(4):547-550.

Peng et al., "Reply to Dr Nielsen: Pericapsular Nerve Group (PENG) block for hip fracture," Reg Anesth Pain Med, Mar. 2019, 44(3):415-416.

Rabbitts et al., "Presurgical psychosocial predictors of acute postsurgical pain and quality of life in children undergoing major surgery," J Pain., Mar. 2015, 16(3):226-234.

Rabbitts et al., "Trajectories of postsurgical pain in children: risk factors and impact of late pain recovery on long-term health outcomes after major surgery," Pain, Nov. 2015, 156(11):2383-2389.

Raja et al., "The revised International Association for the Study of Pain definition of pain: concepts, challenges, and compromises," Pain, Sep. 1, 2020, 161(9):1976-1982.

Rice et al., "Pharmacokinetic Profile and Tolerability of Liposomal Bupivacaine Following a Repeated Dose via Local Subcutaneous Infiltration in Healthy Volunteers," Clin Drug Investig., 2017, 37(3):249-257.

Santos et al., "Is Continuous PENG Block the New 3-in-1?" J Anesth Clin Res 2019, Jun. 28, 2019, 10(6):1000898 , 2 pages.

Shah et al., "Current Trends in Pediatric Spine Deformity Surgery: Multimodal Pain Management and Rapid Recovery," Global Spine J., 2020, 10(3):346-352.

Short et al., "Anatomic Study of Innervation of the Anterior Hip Capsule: Implication for Image-Guided Intervention," Regional Anesthesia and Pain Medicine, Feb. 2018, 43(2):186-192.

Springer et al., "Systemic Safety of Liposomal Bupivacaine in Simultaneous Bilateral Total Knee Arthroplasty," J Arthroplasty., Jan. 2018, 33(1):97-101.

Therapy Services Patient Information [online] "Pubic Rami Fracture," retrieved on Jan. 11, 2023, retrieved from URL <https://www.

(56) References Cited

OTHER PUBLICATIONS uhd.nhs.uk/uploads/about/docs/our_publications/patient_information_leaflets/orthopaedics/Pubic_rami_fracture.pdf>, 12 pages.
Tirotta et al., "Continuous incisional infusion of local anesthetic in pediatric patients following open heart surgery," Pediatr Anaesth., Jun. 2009, 19(6):571-576.
Tran et al.., "Is pericapsular nerve group (PENG) block a true pericapsular block?," Reg Anesth Pain Med, Feb. 2019, 44(2):257.
USFaD, "Pediatric Study Plans: Content of and Process for Submitting Initial Pediatric Study Plans and Amended Initial Pediatric Study Plans Guidance for Industry," US Food and Drug Administration, Jul. 2020, retrieved from URL <https://www.fda.gov/media/86340/download>, 26 pages.
Walker et al., "Complications in Pediatric Regional Anesthesia: An Analysis of More than 100,000 Blocks from the Pediatric Regional Anesthesia Network," Anesthesiology, Oct. 2018, 129(4):721-732.
Yu et al., "Inadvertent quadriceps weakness following the pericapsular nerve group (PENG) block," Reg Anesth Pain Med, May 2019, 44(5):611-613.
[No Author Listed] [online], "Full Prescribing Information—Exparel," exparel.com, revised Mar. 2022, retrieved on Apr. 14, 2022, retrieved from URL <https://www.exparel.com/hcp/prescribing-information.pdf?msclkid=60c82e5b2c231a2fdbe94c034f355fb2&utm_source=bing&utm_medium=cpc&utm_campaign=HCP%20-%20Branded&utm_term=exparel%20dosing%20information&utm_content=Dosage>, 36 pages.
Biotechnology Innovation Organization "Re: Docket No. FDA-2019-N-2514: Standards for Future Opioid Analgesic Approvals and Incentives for New Therapeutics to Treat Pain and Addiction," Nov. 18, 2019, 11 pages.
Delgado et al., "Validation of Digital Visual Analog Scale Pain Scoring With a Traditional Paper-based Visual Analog Scale in Adults," J Am Acad Orthop Surg Glob Res Rev., Mar. 2018, 2(3):e088, 6 pages.
Duzlu et al., "Release Pattern of Liposomal Bupivacaine in Artificial Cerebrospinal Fluid," Turk J Anaesth Reanim., 2016, 44:1-6.
FDA.gov [online] "Methodologies for Determining Opioid Sparing in Acute Pain Models," available on or before Dec. 14, 2019, via Internet Archive: Wayback Machine URL <http://web.archive.org/web/20191214114348/https://www.fda.gov/media/121206/download>, 61 pages.
Ginosar et al., "ED50 and ED95 of Intrathecal Hyperbaric Bupivacaine Coadministered with Opioids for Cesarean Delivery," Anesthesiology, Mar. 2004, 100(3):676-682.
Globalnewswire.com [online], "Pacira—Exparel Achieves Primary and Key Secondary Endpoints in Phase 4 Choice Study in Cesarean Section Patients," Jan. 7, 2020, retrieved on Apr. 11, 2022, retrieved from URL <https://www.globenewswire.com/news-release/2020/01/07/1967140/0/en/EXPAREL-Achieves-Primary-and-Key-Secondary-Endpoints-in-Phase-4-CHOICE-Study-in-Cesarean-Section-Patients.html>, 6 pages.
International Preliminary Report on Patentability in International Appln. No. PCT/US2021/012269, dated Jul. 21, 2022, 23 pages.
International Preliminary Report on Patentability in International Appln. No. PCT/US2021/012275, dated Jul. 12, 2022, 13 pages.
International Preliminary Report on Patentability in International Appln. No. PCT/US2021-012266, dated Jul. 12, 2022, 14 pages.
International Search Report and Written Opinion in International Appln. No. PCT/US2021/012266, dated Apr. 30, 2021, 16 pages.
International Search Report and Written Opinion in International Appln. No. PCT/US2021/012269, dated Mar. 25, 2021, 25 pages.
International Search Report and Written Opinion in International Appln. No. PCT/US2021/012275, dated Mar. 25, 2021, 14 pages.
Joshi et al., "The Safety of Liposome Bupivacaine Following Various Routes of Administration in Animals," Journal of Pain Research, 2015, 8:781-789.
Kim et al., "Preparation of multivesicular liposomes," Biochim. Biophys. Acta—Biomembranes, Mar. 9, 1983, 728(3):339-348.
Laura Giron-Arango et al., "Pericapsular Nerve Group (PENG) Block for Hip Fracture", Reg Anesth Pain Med, 2018, 43:859-863, 5 pages.
Malik et al., "Emerging Roles of Liposomal Bupivacaine in Anesthesia Practice," Journal of Anaesthesiology Clinical Pharmacology, Apr.-Jun. 2017, 33(2):151-156.
Malinovsky et al., "Neurotoxicological Assessment After Intracisternal Injection of Liposomal Bupivacaine in Rabbits," Anesth. Analg., 1997, 85:1331-1336.
Nedeljkovic et al., "Liposomal Bupivacaine Transversus Abdominis Plane Block for Pain After Cesarean Delivery: Results From a Multicenter, Randomized, Double-Blind, Controlled Trial," PowerPoint, Presented at Society for Obstetric Anesthesia and Perinatology 51st Annual Meeting, Phoenix, AZ, May 1-5, 2019, 17 pages.
Nedeljkovic et al., "Transversus Abdominis Plane Block With Liposomal Bupivacaine for Pain After Cesarean Delivery in a Multicenter, Randomized, Double-Blind, Controlled Trial," Anesth. Analg., Dec. 2020, 131(6):1830-1839.
Patel et al., "Brachial Plexus Block with Liposomal Bupivacaine for Shoulder Surgery Improves Analgesia and Reduces Opioid Consumption: Results from a Multicenter, Randomized, Double-Blind, Controlled Trial," Pain Medicine, 2019, 21(2):387-400, 14 pages.
Perets et al., "Intraoperative Infiltration of Liposomal Bupivacaine vs Bupivacaine Hydrochloride for Pain Management in Primary Total Hip Arthroplasty: A Prospective Randomized Trial," The Journal of Arthroplasty, 2018, 33:441-446.
Scott et al., "Acute Toxicity of Ropivacaine Compared with that of Bupivacaine," Anesthesia and Analgesia, Nov. 1, 1989, 69(5):563-569.
www.sec.gov [online], "Pacira BioSciences Reports First Quarter 2019 Revenues of $91.3 Million," May 2019, retrieved on Sep. 30, 2022, retrieved from URL <https://www.sec.gov/Archives/edgar/data/1396814/000139681419000012/pcrx-3312019x991.htm>, 12 pages.
Zel et al., "Neurological and Histological Outcomes After Subarachnoid Injection of a Liposomal Bupivacaine Suspension in Pigs: A Pilot Study," British Journal of Anaesthesia, Mar. 2019, 122(3):379-387.
[No Author Listed] [online], "Adductor Canal Block," RAUKvideos, uploaded on Jan. 29, 2021, retrieved on May 25, 2023, retrieved from URL <https://www.youtube.com/watch?v=DZLjNHkbMtI>, 2 pages [Video Submission].
[No Author Listed] [online], "Adductor Canal Block: What Nerves Are We After?," Regional Anesthesiology and Acute Pain Medicine, uploaded on Oct. 2, 2020, retrieved from internet on May 25, 2023, retrieved from URL <https://www.youtube.com/watch?v=fE4U7JQa2f8>, 2 pages [Video Submission].
Ackmann et al., "Anatomy of the Infrapatellar Branch in Relation to Skin Incisions and as the Basis to Treat Neuropathic Pain by Percutaneous Cryodenervation," Pain Physician Journal, May/Jun. 2014, 17:E229-E348.
Bagaria et al., "The feasibility of direct adductor canal block (DACB) as a part of periarticular injection in total knee arthroplasty," Knee Surgery & Related Research, 2020, 32(48), 7 pages.
Domb et al., "The effect of liposomal bupivacaine injection during total hip arthroplasty: a controlled cohort study," BMC Musculoskeletal Disorders, 2014, 15(310):1-6.
Fiol et al., "Is There A Role for Liposomal Bupivacaine as Part of a Multimodal Strategy Inclusive of Intrathecal Morphine for Post-Cesarean Analgesia? A Retrospective Chart Review Study," Anesth. Pain Res., 2020, 4(2):1-6.
Greenky et al., "Intraoperative Surgeon Administered Adductor Canal Blockade Is Not Inferior to Anesthesiologist Administered Adductor Canal Blockade: A Prospective Randomized Trial," The Journal of Arthroplasty, 2020, 35:1228-1232.
Li et al., "Ultrasound-guided single popliteal sciatic nerve block is an effective postoperative analgesia strategy for calcaneal fracture: a randomized clinical trial," BMC Musculoskeletal Disorders, Jan. 2021, 22(735):1-9.
Matthews et al., "Surgeon-placed peripheral nerve block and continuous non-opioid analgesia in total knee arthroplasty is accessible intraoperatively: A cadaveric study," Journal of ISAKOS, Mar. 2023, 6 pages.

(56) References Cited

OTHER PUBLICATIONS

Matthews, "Continuous Adductor Canal & Periarticular Nerve Block for Total Knee Arthroplasty, Matthews' Placement Guide," Surgical Solutions, 2021, 6 pages.

MayfieldClinic.com [online], "Epidural Steroid Injections (ESI)," Mayfield Brain & Spine, Jul. 2018, retrieved on May 9, 2023, retrieved from URL <https://d3djccaurgtij4.cloudfront.net/pe-esi.pdf>, 3 pages.

Mont et al., "Can Joint Arthroplasty Surgeons Safely Administer Anesthesia?," The Journal of Arthroplasty, 2020, 35:1169.

Pepper et al., "Intraoperative Adductor Canal Block for Augmentation of Periarticular Injection in Total Knee Arthroplasty: A Cadaveric Study," The Journal of Arthroplasty, 2016, 31:2072-2076.

Peterson et al., "Surgeon-Performed High-Dose Bupivacaine Periarticular Injection with Intra-Articular Saphenous Nerve Block is Not Inferior to Adductor Canal Block in Total Knee Arthroplasty," The Journal of Arthroplasty, May 2020, 35:1233-1238.

Rongstad et al., "Popliteal Sciatic Nerve Block for Postoperative Analgesia," Foot & Ankle International, Jul. 1996, 17(7):378-382.

Runge et al., "The Spread of Ultrasound-Guided Injectate From the Adductor Canal to the Genicular Branch of the Posterior Obturator Nerve and the Popliteal," Regional Anesthesia and Acute Pain, Dec. 2017, 42(6):725-730.

Sveom et al., "Ultrasound-Guided Adductor Canal Block Versus Intraoperative Transarticular Saphenous Nerve Block: A Retrospective Analysis," The Journal of Arthroplasty, 2022, 37:S134-S138.

Tak et al., "Continuous adductor canal block is superior to adductor canal block alone or adductor canal block combined with IPACK block (interspace between the popliteal artery and the posterior capsule of knee) in postoperative analgesia and ambulation following continued from U): total knee arthroplasty: randomized control trial," Musculoskeletal Surg., Jun. 2022, 106:155-162.

Tong et al., "Liposomal bupivacaine and clinical outcomes," Best Practice & Research Clinical Anesthesiology, 2014, 28:15-27.

Tran et al., "Evaluation of the proximal adductor canal block injectate spread: a cadaveric study," Reg. Anesth. Pain. Med., 2020, 45:124-130.

Worrell et al., "The Mayo block: an efficacious block for hallux and first metatarsal surgery," AANA Journal, Apr. 1, 1996, 64(2):146-152, Abstract only.

Yee et al., "Quadriceps Weakness After Single-Short Adductor Canal Block," The Journal of Bone and Joint Surgery, 2021, 103(1):30-36.

\* cited by examiner

TREATMENT OF PAIN BY SUBARACHNOID ADMINISTRATION OF SUSTAINED-RELEASE LIPOSOMAL ANESTHETIC COMPOSITIONS

CROSS-REFERENCE TO RELATED APPLICATIONS

This application is a continuation of U.S. application Ser. No. 17/790,426, filed Jun. 30, 2022, which is a National Stage application under 35 U.S.C. § 371 of International Application No. PCT/US2021/012275, filed Jan. 6, 2021, which claims the benefit of U.S. Provisional Application Ser. No. 62/959,550, filed Jan. 10, 2020, U.S. Provisional Application Ser. No. 63/064,760, filed Aug. 12, 2020, and U.S. Provisional Application Ser. No. 63/066,477, filed Aug. 17, 2020, each of which is incorporated by reference herein in its entirety.

BACKGROUND

Extended-release anesthetic formulations of bupivacaine have been developed to prolong the duration of analgesia. Multivesicular liposomal bupivacaine has been approved for single-dose infiltration to produce postsurgical local analgesia and as an interscalene brachial plexus nerve block to produce postsurgical regional analgesia (see EXPAREL® prescribing information, https://www.accessdata.fda.gov/drugsatfda_docs/label/2018/022496s9lbl.pdf). It would also be desirable, however, to provide treatment for pain in a region below the diaphragm that is both safe and effective. Zel et al., *British Journal of Anaesthesia*, 122(3): 1e9 (2018), accepted Oct. 19, 2019, doi: 10.1016/j.bja.2018.10.025, have described subarachnoid administration in pigs, but cautioned that it remains necessary to evaluate the pharmacodynamic properties of liposomal bupivacaine and dose-response before regulatory approval for subarachnoid administration in humans, either in clinical research or practice. Similarly, Joshi et al., who administered liposomal bupivacaine by intrathecal (subarachnoid) injection into dogs, noted that clinical observations from animal studies should be interpreted with appropriate caution. See *Journal of Pain Research* 2015:8 781-789.

Accordingly, there continues to be a need for methods of treating pain in a subject, such as pain in a region below the diaphragm in a subject, such as a human subject.

SUMMARY

In some embodiments provided herein is a method of treating pain in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a subject, the method comprising injecting into the subarachnoid space of the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of treating pain in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing motor block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a subject, the method comprising injecting into the subarachnoid space of the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of inducing motor block in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of inducing sensory block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a subject, the method comprising injecting into the subarachnoid space of the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of inducing sensory block in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the method of treating pain in a subject comprises administering an opioid to the subject following the injection of the pharmaceutical composition into the subarachnoid space of the subject.

In some embodiments, the opioid is administered in a total amount less than 50 mg in the first about 72 hours following the injection of the pharmaceutical composition into the subarachnoid space of the subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a pharmaceutical composition comprising multivesicular liposomes encapsulating bupivacaine phosphate, said multivesicular liposomes comprising:

bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate,
    is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, is not administered to the second subject.

DETAILED DESCRIPTION

In some embodiments provided herein is a method of treating pain in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating pain in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating pain in a subject, the method comprising injecting into the subarachnoid space of the subject a pharmaceutical composition comprising multivesicular liposomes encapsulating bupivacaine phosphate, said multivesicular liposomes comprising:

bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of treating pain in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating pain in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating pain in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a subject in need thereof, the method comprising injecting into the subarachnoid space of the subject a pharmaceutical composition comprising multivesicular liposomes encapsulating bupivacaine phosphate, said multivesicular liposomes comprising:

bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of anesthetizing a subject in need thereof, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a subject in need thereof, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a subject in need thereof, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing pain in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing pain in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing pain in a subject, the method comprising injecting into the subarachnoid space of the subject a pharmaceutical composition comprising multivesicular liposomes encapsulating bupivacaine phosphate, said multivesicular liposomes comprising:

bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing pain in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing pain in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing pain in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of an analgesic, such as an opioid, administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of an analgesic, such as an opioid, administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of an analgesic, such as an opioid, administered to a subject in need thereof, the method comprising injecting into the subarachnoid space of the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing an amount of an analgesic, such as an opioid, administered to a subject in need thereof, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of an analgesic, such as an opioid, administered to a subject in need thereof, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of an analgesic, such as an opioid, administered to a subject in need thereof, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method of reducing a duration of time during which an analgesic, such as an opioid, is administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which an analgesic, such as an opioid, is administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which an analgesic, such as an opioid, is administered to a subject in need thereof, the method comprising injecting into the subarachnoid space of the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing a duration of time during which an analgesic, such as an opioid, is administered to a subject in need thereof, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which an analgesic, such as an opioid, is administered to a subject in need thereof, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which an analgesic, such as an opioid, is administered to a subject in need thereof, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the analgesic, such as an opioid, is administered to the subject, the analgesic is administered following a surgical procedure in the subject. In some embodiments the analgesic reduces pain in the subject following the surgical procedure.

In some embodiments provided herein is a method of reducing an amount of a non-opioid analgesic administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of a non-opioid analgesic administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of a non-opioid analgesic administered to a subject in need thereof, the method comprising injecting into the subarachnoid space of the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing an amount of a non-opioid analgesic administered to a subject in need thereof, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of a non-opioid analgesic administered to a subject in need thereof, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of a non-opioid analgesic administered to a subject in need thereof, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the non-opioid analgesic is administered to the subject, the non-opioid analgesic is administered following a surgical procedure in the subject. In some embodiments the non-opioid analgesic reduces pain in the subject following the surgical procedure.

In some embodiments provided herein is a method of reducing a duration of time during which a non-opioid analgesic is administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which a non-opioid analgesic is administered to a subject in need thereof, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which a non-opioid analgesic is administered to a subject in need thereof, the method comprising injecting into the subarachnoid space of the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing a duration of time during which a non-opioid analgesic is administered to a subject in need thereof, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which a non-opioid analgesic is administered to a subject in need thereof, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which a non-opioid analgesic is administered to a subject in need thereof, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some more particular embodiments of the methods where the non-opioid analgesic is administered to the subject, the non-opioid analgesic is administered following a surgical procedure in the subject. In some embodiments the non-opioid analgesic reduces pain in the subject following the surgical procedure.

In some embodiments provided herein is a method of inducing motor block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing motor block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing motor block in a subject, the method comprising injecting into the subarachnoid space of the subject a pharmaceutical composition comprising multivesicular liposomes encapsulating bupivacaine phosphate, said multivesicular liposomes comprising:

bupivacaine or a salt thereof;
    phosphoric acid;
    a lipid component comprising at least one amphipathic lipid and at least one neutral lipid lacking a hydrophilic head group; and,
    optionally, a cholesterol and/or a plant sterol wherein said multivesicular liposomes are made by a process comprising:
    a) preparing a first aqueous component comprising phosphoric acid;
    b) preparing a lipid component comprising at least one organic solvent, at least one amphipathic lipid, and at least one neutral lipid lacking a hydrophilic head group;
    c) mixing said first aqueous component and said lipid component to form a water-in-oil emulsion, wherein at least one component comprises bupivacaine or a salt thereof;
    d) mixing said water-in-oil emulsion with a second aqueous component to form solvent spherules; and
    e) removing the organic solvent from the solvent spherules to form multivesicular liposomes encapsulating bupivacaine phosphate.

In some embodiments provided herein is a method of inducing motor block in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing motor block in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing motor block in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the motor block has a shorter duration than the motor block induced by injecting into the subarachnoid space of the subject non-liposomal bupivacaine containing the same amount of bupivacaine as the pharmaceutical composition disclosed herein. In some embodiments, injecting into the subarachnoid space of the subject a pharmaceutical composition as disclosed herein induces a motor block having a duration of about 12 hours or less, or from about 12 hours to about 24 hours, or from about 24 hours to about 48 hours, or from about 48 hours to about 72 hours.

In some embodiments provided herein is a method of inducing sensory block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of inducing sensory block in a subject, the method comprising injecting into the subarachnoid space of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of inducing sensory block in a subject, the method comprising injecting into the subarachnoid space of the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of inducing sensory block in a subject, the method comprising injecting into the subarachnoid space of the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of inducing sensory block in a subject, the method comprising injecting into the subarachnoid space of the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of inducing sensory block in a subject, the method comprising injecting into the subarachnoid space of the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the sensory block has a longer duration than the motor block induced by injecting into the subarachnoid space of the subject the same amount of the pharmaceutical composition.

In some embodiments, the sensory block has a longer duration than the sensory block induced by injecting into the subarachnoid space of the subject non-liposomal bupivacaine containing the same amount of bupivacaine as the pharmaceutical composition disclosed herein. In some embodiments, injecting into the subarachnoid space of the subject a pharmaceutical composition as disclosed herein induces a sensory block having a duration of from about 24 hours to about 72 hours, such as from about 24 hours to about 48 hours, such as from about 48 hours to about 72 hours. In some embodiments, injecting into the subarachnoid space of the subject a pharmaceutical composition described herein reduces pain for a longer period of time than the duration of the motor block induced by injecting into the subarachnoid space of the subject the same amount of the pharmaceutical composition. Accordingly, in some embodiments of the method comprising injecting into the subarachnoid space of the subject a pharmaceutical composition described herein, wherein an analgesic, such as an opioid, or such as a non-opioid analgesic, is administered to the subject, the analgesic is administered after offset of the motor block.

In some embodiments the at least one polyhydroxy carboxylic acid is selected from the group consisting of glucuronic acid, gluconic acid and tartaric acid.

In some embodiments the amphipathic lipid is selected from the group consisting of phosphatidylcholines, phosphatidylethanolamines, sphingomyelins, lysophosphatidylcholines, lysophosphatidylethanolamines, phosphatidylglycerols, phosphatidylserines, phosphatidylinositols, phosphatidic acids, cardiolipins, diacyl dimethylammonium propanes, and stearylamines.

In some embodiments the neutral lipid comprises at least one triglyceride.

In some embodiments the method comprises administering a therapeutically effective amount of the pharmaceutical composition.

In some embodiments the pharmaceutical composition comprises a therapeutically effective amount of bupivacaine phosphate. In some embodiments the amount of the pharmaceutical composition described herein is equivalent to from about 100 mg to about 300 mg of bupivacaine. In some embodiments the amount of the pharmaceutical composition described herein is equivalent to from about 133 mg to about 266 mg of bupivacaine. In some embodiments the amount of the pharmaceutical composition described herein is equivalent to from about 10 mg to about 70 mg of bupivacaine, such as from about 13.3 mg to about 66.5 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine.

In some embodiments, the pain that may be treated according to the methods disclosed herein is in a region below the diaphragm. In some embodiments, the pain is selected from abdomen pain, lower back pain, hip pain, pelvic pain, femur pain, knee pain, foot pain, and ankle pain.

In some embodiments, the pain is abdomen pain.
In some embodiments, the pain is lower back pain.
In some embodiments, the pain is hip pain.
In some embodiments, the pain is pelvic pain.
In some embodiments, the pain is femur pain.
In some embodiments, the pain is knee pain.
In some embodiments, the pain is foot pain.
In some embodiments, the pain is ankle pain.

In some embodiments the method comprises administering the pharmaceutical composition by epidural injection.

In some embodiments the method does not comprise administering the pharmaceutical composition by epidural injection.

In some embodiments the method comprises administering an analgesic, such as an opioid, to the subject following the injection of the pharmaceutical composition into the subarachnoid space of the subject.

In some embodiments of the methods herein, the opioid is administered in a total amount less than 200 mg, such as less than 100 mg, such as less than 50 mg, such as less than 25 mg, such as less than 15 mg, in the first about 72 hours following the injection of the pharmaceutical composition into the subarachnoid space of the subject. In some embodiments, the opioid is oxycodone and the method comprises administering oxycodone in a total amount less than 15 mg·in the first about 72 hours following the injection of the pharmaceutical composition into the subarachnoid space of the subject. In some embodiments, the method comprises administering one or more morphinans to the subject. In some embodiments, the method comprises administering morphine to the subject. In some more particular embodiments, the morphine is administered to the subject for up to 72 hours following the injection of the pharmaceutical composition into the subarachnoid space of the subject.

In some embodiments, the method comprises administering one or more analgesics to the subject, such as one or more non-opioid analgesics, such as one or more NSAIDs to the subject, following the injection of the pharmaceutical composition into the subarachnoid space of the subject. In some embodiments, the method comprises administering one or more of ketorolac, acetaminophen or ibuprofen to the subject. In some embodiments, the method comprises administering two or more of ketorolac, acetaminophen or ibuprofen to the subject. In some embodiments, the method comprises administering ketorolac, acetaminophen and ibuprofen to the subject. In some more particular embodiments, the analgesic, such as the NSAID, such as the one or more of ketorolac, acetaminophen or ibuprofen, is administered to the subject for up to 72 hours following the injection of the pharmaceutical composition into the subarachnoid space of the subject.

In some embodiments, the subject has an AUC for VAS pain intensity scores over the first 72 hours following the injection of the pharmaceutical composition into the subarachnoid space of the subject of from about 100 to about 200, such as about 125 to 175, such as about 140 to 160, such as about 150, such as about 147.9.

In some embodiments of the methods herein, the subject has a pruritus score as determined by the 5-D itch scale of about 10 to 20, such as about 12 to 18, such as about 13 to 16, such as about 14 to 15.

In some embodiments of the methods herein, the plasma Cmax of bupivacaine in the subject is about 150 ng/mL to about 250 ng/mL, such as about 175 ng/mL to about 225 ng/mL, such as about 200 ng/mL, such as about 210 mg/mL, for an amount of the pharmaceutical composition described herein that is equivalent to about 133 mg of bupivacaine. In some embodiments, the Cmax occurs after about 48 hours following the injection of the multivesicular liposome composition into the subarachnoid space of the subject. In some embodiments, the Cmax occurs after about 72 hours following the injection of the multivesicular liposome composition into the subarachnoid space of the subject.

In some embodiments of the methods herein, the plasma Cmax of bupivacaine in the subject is about 300 ng/mL to about 550 ng/mL, such as about 350 ng/mL to about 500 ng/mL, such as about 450 mg/mL, such as about 460 ng/mL, for an amount of the pharmaceutical composition described herein that is equivalent to about 266 mg of bupivacaine. In some embodiments, the Cmax occurs after about 48 hours following the injection of the multivesicular liposome composition into the subarachnoid space of the subject. In some embodiments, the Cmax occurs after about 72 hours following the injection of the multivesicular liposome composition into the subarachnoid space of the subject.

In some embodiments of the methods herein, the plasma Cmax of bupivacaine in the subject is less than about 850 ng/mL, such as less than about 800 ng/mL, such as less than about 750 ng/mL, such as less than about 700 ng/mL, such as less than about 650 ng/mL, such as less than about 600 ng/mL.

In some embodiments, the subject is a human.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
    a) preparing a first aqueous component comprising phosphoric acid;

b) preparing a lipid component comprising at least one organic solvent, at least one amphipathic lipid, and at least one neutral lipid lacking a hydrophilic head group;

c) mixing said first aqueous component and said lipid component to form a water-in-oil emulsion, wherein at least one component comprises bupivacaine or a salt thereof;

d) mixing said water-in-oil emulsion with a second aqueous component to form solvent spherules; and e) removing the organic solvent from the solvent spherules to form multivesicular liposomes encapsulating bupivacaine phosphate, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subject.

In some embodiments of the method of treating pain in a subject, wherein the subject is a first subject, in the first about 72 hours following injection of the pharmaceutical composition into the subarachnoid space of the first subject the opioid is administered to the first subject in a total amount that is lower than the total amount of an opioid that is administered to a second subject in the first about 72 hours following injection into the subarachnoid space of the second subject of non-liposomal bupivacaine containing the same amount of bupivacaine as the pharmaceutical composition, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, is not administered to the second subject.

In some embodiments, the opioid that is administered to the first subject and the opioid that is administered to the second subject are the same. In some embodiments, the opioid that is administered to the first subject and the opioid that is administered to the second subject are different.

In some embodiments of the method of treating pain in a subject, wherein the subject is a first subject, in the first about 72 hours following injection of the pharmaceutical composition into the subarachnoid space of the first subject, the opioid is administered to the first subject in a total amount that is lower than the total amount of an opioid that is administered to each of a plurality of second subjects in the first about 72 hours following respective injection into the subarachnoid space of each of the second subjects of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subjects.

In some embodiments of the method of treating pain in a subject, wherein the subject is a first subject, in the first about 72 hours following injection of the pharmaceutical composition into the subarachnoid space of the first subject, the opioid is administered to the first subject in a total amount that is lower than the total amount of an opioid that is administered to each of a plurality of second subjects in the first about 72 hours following respective injection into the subarachnoid space of each of the second subjects of non-liposomal bupivacaine containing the same amount of bupivacaine as the pharmaceutical composition, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subjects.

In some embodiments of the method of treating pain in a subject, wherein the subject is a first subject, in the first about 72 hours following injection of the pharmaceutical composition into the subarachnoid space of the first subject, the opioid is administered to the first subject in a total amount that is lower than the total amount of an opioid that is administered to each of a plurality of second subjects in the first about 72 hours following respective injection into the subarachnoid space of each of the second subjects of non-liposomal bupivacaine containing the same amount of bupivacaine as the pharmaceutical composition, wherein a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  is not administered to the second subjects.

In some embodiments of the method of treating pain in a subject, wherein the subject is a first subject, in the first about 72 hours following injection of the pharmaceutical composition into the subarachnoid space of the first subject, the opioid is administered to the first subject in a total amount that is lower than the total amount of an opioid that is administered to each of a plurality of second subjects in the first about 72 hours following respective injection into the subarachnoid space of each of the second subjects of non-liposomal bupivacaine containing the same amount of bupivacaine as the pharmaceutical composition, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subjects.

In some embodiments of the method of treating pain in a subject, wherein the subject is a first subject, in the first about 72 hours following injection of the pharmaceutical composition into the subarachnoid space of the first subject, the opioid is administered to the first subject in a total amount that is lower than the total amount of an opioid that is administered to each of a plurality of second subjects in the first about 72 hours following respective injection into the subarachnoid space of each of the second subjects of non-liposomal bupivacaine containing the same amount of bupivacaine as the pharmaceutical composition, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subjects.

In some embodiments of the method of treating pain in a subject, wherein the subject is a first subject, in the first about 72 hours following injection of the pharmaceutical composition into the subarachnoid space of the first subject, the opioid is administered to the first subject in a total amount that is lower than the total amount of an opioid that is administered to each of a plurality of second subjects in the first about 72 hours following respective injection into the subarachnoid space of each of the second subjects of non-liposomal bupivacaine containing the same amount of bupivacaine as the pharmaceutical composition, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, is not administered to the second subjects.

In some embodiments, the opioid that is administered to the first subject and the opioid that is administered to at least one of the second subjects are the same. In some embodiments, the opioid that is administered to the first subject and the opioid that is administered to at least one of the second subjects are different. In some embodiments, the opioid that is administered to the first subject and the opioids that are administered to the second subjects are the same. In some embodiments, the opioid that is administered to the first subject and the opioids that are administered to the second subjects are different. In some embodiments, the total amount of an opioid that is administered to each of a plurality of second subjects is a mean total amount.

In some embodiments of the methods herein, the opioid is administered to the first subject in a total amount that is at least about 20% lower, such as at least about 30% lower, such as at least about 40% lower, such as at least about 50% lower than the total amount of the opioid that is administered to the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 72 hours following injection of the pharmaceutical composition into the subarachnoid space of the first subject the opioid is administered to the first subject in a total amount that is at least about 20% lower, such as at least about 30% lower, such as at least about 40% lower, such as at least about 50% lower than the total amount of the opioid that is administered to the second subject in the first about 72 hours following injection into the subarachnoid space of the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 24 hours following injection of the pharmaceutical composition into the subarachnoid space of the first subject the opioid is administered to the first subject in a total amount that is lower than the total amount of the opioid that is administered to the second subject in the first about 24 hours following injection into the subarachnoid space of the second subject of non-liposomal bupivacaine. In some embodiments of the methods herein, in the first about 24 hours following injection of the pharmaceutical composition into the subarachnoid space of the first subject the opioid is administered to the first subject in a total amount that is at least about 20% lower, such as at least about 30% lower, such as at least about 40% lower, such as at least about 50% lower than the total amount of the opioid that is administered to the second subject in the first about 24 hours injection into the subarachnoid space of the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 48 hours following injection of the pharmaceutical composition into the subarachnoid space of the first subject the opioid is administered to the first subject in a total amount that is lower than the total amount of the opioid that is administered to the second subject in the first about 48 hours following injection into the subarachnoid space of the second subject of non-liposomal bupivacaine. In some embodiments of the methods herein, in the first about 48 hours following injection of the pharmaceutical composition into the subarachnoid space of the first subject the opioid is administered to the first subject in a total amount that is at least about 20% lower, such as at least about 30% lower, such as at least about 40% lower, such as at least about 50% lower than the total amount of the opioid that is administered to the second subject in the first about 48 hours following injection into the subarachnoid space of the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 7 days following injection of the pharmaceutical composition into the subarachnoid space of the first subject the opioid is administered to the first subject in a total amount that is lower than the total amount of the opioid that is administered to the second subject in the first about 7 days following injection into the subarachnoid space of the second subject of non-liposomal bupivacaine. In some embodiments of the methods herein, in the first about 7 days following injection of the pharmaceutical composition into the subarachnoid space of the first subject the opioid is administered to the first subject in a total amount that is at least about 20% lower, such as at least about 30% lower, such as at least about 40% lower, such as at least about 50% lower than the total amount of the opioid that is administered to the second subject in the first about 7 days following injection into the subarachnoid space of the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 14 days following injection of the pharmaceutical composition into the subarachnoid space of the first subject the opioid is administered to the first subject in a total amount that is lower than the total amount of the opioid that is administered to the second subject in the first about 14 days following injection into the subarachnoid space of the second subject of non-liposomal bupivacaine. In some embodiments of the methods herein, in the first about 14 days following injection of the pharmaceutical composition into the subarachnoid space of the first subject the opioid is administered to the first subject in a total amount that is at least about 20% lower, such as at least about 30% lower, such as at least about 40% lower, such as at least about 50% lower than the total amount of the opioid that is administered to the second subject in the first about 14 days following injection into the subarachnoid space of the second subject of non-liposomal bupivacaine. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, the first subject has an AUC for VAS pain intensity scores over the first 72 hours following injection of the pharmaceutical composition into the subarachnoid space of the first subject of from about 100 to about 200, such as about 125 to 175, such as about 140 to 160, such as about 150, such as about 147.9; and the second subject has an AUC for VAS pain intensity scores over the first 72 hours following injection into the subarachnoid space of the second subject of non-liposomal bupivacaine of from about 150 to about 250, such as about 165 to 200, such as about 170 to 190, such as about 175 to 180, such as about 178.5.

In some embodiments of the methods herein, the first subject has an AUC for VAS pain intensity scores over the first 72 hours following injection of the pharmaceutical composition into the subarachnoid space of the first subject that is at least about 10% lower, such as at least about 17% lower, such as about 27% to about 25% lower, such as at least about 25% lower, than the AUC for VAS pain intensity scores for the second subject over the first 72 hours following injection into the subarachnoid space of the second subject of non-liposomal bupivacaine. In some embodiments the first subject has an AUC for VAS pain intensity scores over the first 72 hours following injection of the pharmaceutical composition into the subarachnoid space of the first subject that is up to 100% lower (that is, the AUC is 0), such as up to 90% lower, such as up to 80% lower, such as up to 70% lower, such as up to 60% lower, than the AUC for VAS pain intensity scores for the second subject.

In some embodiments of the methods herein, the first subject has a pruritus score as determined by the 5-D itch scale that is lower than the pruritus score for the second subject.

In some embodiments of the methods herein, the plasma concentration of bupivacaine in the first subject after about 120 hours following injection of the pharmaceutical composition into the subarachnoid space of the first subject is at least about 10%, such as least about 20% higher, such as at least about 30% higher, such as at least about 40% higher, such as 50% higher than the plasma concentration of bupivacaine in the second subject after about 120 hours following injection into the subarachnoid space of the second subject of non-liposomal bupivacaine. In some embodiments, the plasma concentration is up to 500% higher, such as up to 400% higher, such as up to 300% higher, such as up to 200% higher, such as up to 100% higher, than the plasma concentration in the second subject.

In some embodiments, the method does not comprise administering an analgesic, such as an opioid, to the subject following the injection of the pharmaceutical composition into the subarachnoid space of the subject.

In some embodiments, the method does not comprise administering one or more morphinans to the subject following the injection of the pharmaceutical composition into the subarachnoid space of the subject. In some embodiments, the method does not comprise administering morphine to the subject following the injection of the pharmaceutical composition into the subarachnoid space of the subject.

In some embodiments, the method does not comprise administering an opioid to the first subject following the injection of the pharmaceutical composition into the subarachnoid space of the subject.

In some embodiments, the method does not comprise administering one or more morphinans to the first subject. In some embodiments, the method does not comprise administering morphine to the first subject.

In some embodiments, the first subject is a human and the second subject is a human.

In some embodiments, the method comprises injecting into the subarachnoid space of the subject an amount of a pharmaceutical composition described herein that is equivalent to about 10 to about 300 mg of bupivacaine. In some embodiments the pharmaceutical composition comprises an amount equivalent to from about 10 mg to about 300 mg of bupivacaine. In some embodiments the pharmaceutical composition comprises an amount equivalent to from about 133 mg to about 266 mg of bupivacaine. In some embodiments the pharmaceutical composition comprises an amount equivalent to from about 10 mg to about 70 mg of bupivacaine. In some embodiments the pharmaceutical composition comprises an amount equivalent to from about 20 mg to about 60 mg of bupivacaine. In some embodiments the pharmaceutical composition comprises an amount equivalent to from about 20 mg to about 50 mg of bupivacaine. In some embodiments the pharmaceutical composition comprises an amount equivalent to from about 20 mg to about 40 mg of bupivacaine. In some embodiments the pharmaceutical composition comprises an amount equivalent to from about 20 mg to about 30 mg of bupivacaine. In some embodiments the pharmaceutical composition comprises an amount equivalent to from about 30 mg to about 60 mg of bupivacaine. In some embodiments the pharmaceutical composition comprises an amount equivalent to from about 30 mg to about 50 mg of bupivacaine. In some embodiments the pharmaceutical composition comprises an amount equivalent to from about 30 mg to about 40 mg of bupivacaine. In some embodiments the amount of the pharmaceutical composition described herein is equivalent to from about 10 mg to about 70 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine.

In some embodiments the amount of the pharmaceutical composition described herein is equivalent to 13.3 mg of bupivacaine. In some embodiments the amount of the pharmaceutical composition described herein is equivalent to 26.6 mg of bupivacaine. In some embodiments the amount of the pharmaceutical composition described herein is equivalent to 39.9 mg of bupivacaine. In some embodiments the amount of the pharmaceutical composition described herein is equivalent to 53.2 mg of bupivacaine.

In some embodiments, the method comprises administering one or more non-opioid analgesics to the subject. In some embodiments, the one or more non-opioid analgesics are one or more NSAIDs. In some embodiments, the one or more non-opioid analgesics are one or more of ketorolac, acetaminophen or ibuprofen. Thus, in some embodiments, the method comprises administering one or more of ketorolac, acetaminophen or ibuprofen to the subject, wherein the one or more of ketorolac, acetaminophen or ibuprofen, is administered to the subject for up to 72 hours following the injection of the pharmaceutical composition into the subarachnoid space of the subject in the following amounts:

IV ketorolac 15 mg once at the time of skin incision closure and prior to the TAP infiltration Intravenous (IV) acetaminophen 1000 mcg at the time of skin incision closure Scheduled oral (PO) acetaminophen 650 mg at the end of surgery and every 6 hours (q6 h) for up to 72 hours Scheduled PO ibuprofen 600 mg at the end of surgery and q6 h for up to 72 hours In some embodiments, the method comprises administering an opioid to a subject following the injection of the pharmaceutical composition into the subarachnoid space of the subject, wherein one or more opioids are administered in the following amounts:

oral immediate-release oxycodone at 5-10 mg every 4 hours or as needed

IV morphine at 1-2 mg or hydromorphone initiated at 0.3-0.5 mg every 4 hours or as needed In some embodiments, injecting into the subarachnoid space of the subject the pharmaceutical composition disclosed herein provides a $T_{max}$ of bupivacaine in plasma that is higher than the $T_{max}$ of bupivacaine in plasma provided by the injection of non-liposomal bupivacaine containing the same amount of bupivacaine as the pharmaceutical composition disclosed herein into the subarachnoid space of the subject. In some embodiments $T_{max}$ of bupivacaine in plasma provided by the injection of the pharmaceutical composition disclosed herein is about 12 hours to about 36 hours, such as about 24 hours. In some embodiments $T_{max}$ of non-liposomal bupivacaine in plasma is about 20 minutes to about 1 hour, such as about 30 minutes.

In some embodiments, injecting into the subarachnoid space of the subject the pharmaceutical composition disclosed herein provides a $T_{max}$ of bupivacaine in plasma that is higher than the $T_{max}$ of bupivacaine in plasma provided by the injection of non-liposomal bupivacaine containing the same amount of bupivacaine as the pharmaceutical composition disclosed herein into the subarachnoid space of the subject.

In some embodiments, injecting into the subarachnoid space of the subject the pharmaceutical composition disclosed herein provides a $C_{max}$ of bupivacaine in plasma that is lower than the $C_{max}$ of bupivacaine in plasma provided by the injection of non-liposomal bupivacaine containing the same amount of bupivacaine as the pharmaceutical composition disclosed herein into the subarachnoid space of the subject.

In some embodiments, injecting into the subarachnoid space of the subject the pharmaceutical composition disclosed herein provides an apparent terminal elimination half-life (t½el) of bupivacaine in plasma that is higher than the t½el of bupivacaine in plasma provided by the injection of non-liposomal bupivacaine containing the same amount of bupivacaine as the pharmaceutical composition disclosed herein into the subarachnoid space of the subject.

In some embodiments, injecting into the subarachnoid space of the subject the pharmaceutical composition disclosed herein provides an apparent volume of distribution (Vd) of bupivacaine in plasma that is lower than the Vd of bupivacaine in plasma provided by the injection of non-liposomal bupivacaine containing the same amount of bupivacaine as the pharmaceutical composition disclosed herein into the subarachnoid space of the subject.

In some embodiments, injecting into the subarachnoid space of the subject the pharmaceutical composition induces an onset of motor block in the subject after a shorter period of time than is provided by the injection of non-liposomal bupivacaine containing the same amount of bupivacaine as the pharmaceutical composition disclosed herein into the subarachnoid space of the subject.

In some embodiments, duration of motor block in the subject is shorter than duration of motor block in the subject when non-liposomal bupivacaine containing the same amount of bupivacaine as the pharmaceutical composition disclosed herein is administered to the subarachnoid space of the subject.

In some embodiments, to test onset and duration of motor effects, the following assessments are performed:
Handheld dynamometer
Bromage scale
Berg balance scale (7 item)

Thus, in some aspects of embodiments herein, the onset of the motor block is determined with a handheld dynamometer. In some aspects of embodiments herein, the onset of the motor block is determined according to the Bromage scale. In some aspects of embodiments herein, the onset of the motor block is determined according to the Berg balance scale.

Thus, in some aspects of embodiments herein, the duration of the motor block is determined with a handheld dynamometer. In some aspects of embodiments herein, the duration of the motor block is determined according to the Bromage scale. In some aspects of embodiments herein, the duration of the motor block is determined according to the Berg balance scale.

In some embodiments, onset and offset of motor block are evaluated using a handheld dynamometer at knee extension. In some embodiments, onset of motor block is defined as the earliest time point after injection into the subarachnoid space of the subject of the pharmaceutical composition when a 20% or greater weakness from baseline is noted. In some embodiments offset of motor block is defined as the earliest time point after onset of motor block when less than 20% weakness from baseline is noted. Duration of motor block is the time between onset and offset of motor block.

In some embodiments, injecting into the subarachnoid space of the subject the pharmaceutical composition induces an onset of sensory block in the subject after a longer period of time than is provided by the injection of non-liposomal bupivacaine containing the same amount of bupivacaine as the pharmaceutical composition disclosed herein into the subarachnoid space of the subject.

In some embodiments, duration of sensory block in the subject is longer than duration of sensory block in the subject when non-liposomal bupivacaine containing the same amount of bupivacaine as the pharmaceutical composition disclosed herein is administered to the subarachnoid space of the subject.

In some embodiments, onset and segmental spread of sensory block are evaluated by testing the sensitivity to pinprick and cold in the S1, L2, L3, L4, T10-11, T7-8, and T4 dermatomes. In some embodiments, onset of sensory block is the earliest time point after injection into the subarachnoid space of the subject of the pharmaceutical composition at which loss of sensation is noted below L2, such as S1, L3 and/or L4. In some embodiments, offset of sensory block will be defined as the earliest time point after onset of block at which recovery of sensation at L4 and S1 is noted.

Duration of sensory block is the time between onset and offset of sensory block.

Thus, in some aspects of embodiments herein, the onset of the sensory block is determined by testing the sensitivity to pinprick in one or more of the S1, L2, L3, L4, T10-11, T7-8, and T4 dermatomes, such as, for example, the S1, L3 and L4 dermatomes. In some aspects of embodiments herein, the onset of the sensory block is determined by testing the sensitivity to cold in one or more of the S1, L2, L3, L4, T10-11, T7-8, and T4 dermatomes, such as, for example, the S1, L3 and L4 dermatomes.

Thus, in some aspects of embodiments herein, the offset of the sensory block is determined by testing recovery of sensation in one or more of the S1, L2, L3, L4, T10-11, T7-8, and T4 dermatomes, such as, for example, the S1, L3 and L4 dermatomes.

In some embodiments, the injection of the pharmaceutical composition into the subarachnoid space of the subject is performed in a manner analogous to that described in Zel et al., *British Journal of Anaesthesia*, 122(3): 1e9 (2018), accepted Oct. 19, 2019, doi: 10.1016/j.bja.2018.10.025, incorporated by reference herein in its entirety.

In some embodiments of any of the methods disclosed herein, the method produces postsurgical local analgesia.

In some embodiments of any of the methods disclosed herein, the method produces postsurgical regional analgesia.

In some embodiments of any of the methods disclosed herein, the subject does not experience neurological side effects.

In some embodiments of any of the methods disclosed herein, the subject does not experience cardiac side effects.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

As used herein, the terms "subarachnoid" and "intrathecal", for example in the recitations "subarachnoid injection" and "intrathecal injection", are used interchangeably. Subarachnoid injection refers to injection below vertebral segment L2.

As used herein, "injecting into the subarachnoid space" a composition means administering the composition by subarachnoid injection. Similarly, "injection into the subarachnoid space" of a composition means administration of the composition by subarachnoid injection.

The term "therapeutically effective" as it pertains to bupivacaine or a salt thereof, such as bupivacaine phosphate, present in the pharmaceutical compositions described herein, means that an anesthetic present in the first aqueous phase within the multivesicular liposome is released in a manner sufficient to achieve a particular level of anesthesia. Exact dosages will vary depending on such factors as the particular anesthetic, as well as patient factors such as age, sex, general condition, and the like. Those of skill in the art can readily take these factors into account and use them to establish effective therapeutic concentrations without resort to undue experimentation.

As used herein, "non-liposomal bupivacaine" refers to bupivacaine that is not in liposomal form. For example, "non-liposomal bupivacaine" refers to bupivacaine that is not comprised in a multivesicular liposome. The term "non-liposomal bupivacaine" also encompasses a composition comprising bupivacaine that is not in liposomal form.

As used herein, a "VAS pain intensity score" refers to the Visual Analog Scale pain intensity score described in Delgado et al., *J Am Acad Orthop Surg Glob Res Rev.* 2018

March; 2(3): e088 published online 2018 Mar. 23. doi: 10.5435/JAAOSGlobal-D-17-00088, incorporated by reference herein in its entirety.

In some embodiments the compositions used in the methods disclosed herein comprise a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments the compositions used in the methods disclosed herein comprise: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments the compositions used in the methods disclosed herein comprise multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments the compositions used in the methods disclosed herein are multivesicular liposomal particle pharmaceutical compositions made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein the compositions used in the methods disclosed herein are compositions of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein the compositions used in the methods disclosed herein are compositions comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments the aqueous phase further comprises hydrochloric acid.

Multivesicular liposomes (or "MVL", which is used herein to refer to a multivesicular liposome or a plurality of multivesicular liposomes) are lipid vesicles having multiple non-concentric internal aqueous chambers having internal membranes distributed as a network throughout the MVL. The chambers may contain acids which are effective to enable the encapsulation of bupivacaine or a salt thereof and to modulate its release rate. A preparation of MVL is described, for example, in Kim et al., Biochim. Biophys. Acta 728, 339-348, 1983. In some embodiments, a MVL is prepared in accordance with a process as described in U.S. Pat. No. 9,192,575, incorporated by reference herein in its entirety. In some embodiments, a MVL is prepared in accordance with a process as described in U.S. Pat. No. 8,182,835, incorporated by reference herein in its entirety. In some embodiments, a MVL is prepared in accordance with a process as described in U.S. Pat. No. 8,834,921, incorporated by reference herein in its entirety. In some embodiments, a MVL is prepared in accordance with a process as described in U.S. Pat. No. 9,205,052, incorporated by reference herein in its entirety.

In some embodiments the multivesicular liposomes ("MVL") are made by the following process. A "water-in-oil" type emulsion containing a non-hydrohalic acid salt of bupivacaine, such as bupivacaine phosphate, is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamines.

Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

Many types of volatile organic solvents can be used in the present invention, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the compositions of the present invention.

Optionally, other components are included in the lipid phase. Among these are cholesterol or plant sterols.

The first aqueous phase includes bupivacaine or a salt thereof, such as bupivacaine phosphate, at least one polyhydroxy carboxylic acid, and at least one di- or tri-protic mineral acid. In some embodiments, also included is hydrochloric acid. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, bupivacaine or a salt thereof, such as bupivacaine phosphate, is encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the bupivacaine or a salt thereof, such as bupivacaine phosphate, dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

In some embodiments, an MVL is prepared in accordance with a process as described in U.S. Pat. No. 10,398,648, incorporated by reference herein in its entirety. In some embodiments, a MVL is prepared in accordance with a process as described in U.S. Pat. No. 9,585,838 incorporated by reference herein in its entirety.

In some embodiments, a MVL is prepared in accordance with a process as described in US 2011-0250264, US 2013-0306759, US 2013-0177634, US 2013-0177633, US 2013-0177635, US 2013-0195965, US 2013-0177636, US 2013-0183373, US 2013-0177638, US 2013-0177637, US 2013-0183372, US 2013-0183375, US 2016-0361260 or US 2018-0092847, each of which is incorporated by reference herein in its entirety.

EXAMPLES

Example 1— Clinical Trial

On Day 1, eligible subjects will be randomized in blocks of 5, in a ratio of 3:1:1 to receive EXPAREL® or bupivacaine or placebo (saline) injection, respectively. EXPAREL® is the trade name for the pharmaceutical composition disclosed herein. Starting with treatment cohort 1, healthy volunteers will be randomized to the 3 treatment arms within cohorts. Each cohort will consist of 10 subjects (6 EXPAREL®, 2 bupivacaine and 2 placebo).

In each cohort, within the EXPAREL® arm, subjects will be randomized 2:1 with 4 subjects undergoing cerebrospinal fluid (CSF) tap and 2 subjects not undergoing CSF tap.

Subjects who are not undergoing CSF tap, will undergo a CSF sham draw to prevent subject bias. This will allow for the full characterization of the pharmacodynamic profile of the drug in these subjects without risk of drug removal from the CSF.

For those subjects randomized to the EXPAREL® arm—the dose of MVL will be determined by the cohort. Starting at 1 mL (13.3 mg) for cohort 1, the volume of EXPAREL® will be increased by 1 mL in each subsequent cohort for a maximum of 4 mL (53.2 mg), as described in the table below.

In each cohort, subjects randomized to the bupivacaine arm will receive 15 mg of plain bupivacaine HCL (the equivalent of 13.3 mg bupivacaine base) providing a 1:1 reference to the starting dose level chosen for EXPAREL® The decision to proceed to the next cohort will be made following a full review of the safety, PK, and PD (sensory and motor) data from the previous completed cohort(s).

The following summarizes the treatment for each cohort:

EXPAREL® Arm:

For those subjects randomized to EXPAREL® arm, the dose of EXPAREL® will be determined by the cohort. Starting at 1 mL (13.3 mg) for cohort 1, the volume of EXPAREL® will be increased by 1 mL in each subsequent cohort for a maximum of 4 mL (53.2 mg), as described in the table below.

| Treatment Cohorts | Volume (mL) of EXPAREL ® | Dose (mg) of bupivacaine |
|---|---|---|
| 1 | 1 | 13.3 |
| 2 | 2 | 26.6 |
| 3 | 3 | 39.9 |
| 4 | 4 | 53.2 |

Bupivacaine Arm:

In each cohort, subjects randomized to the bupivacaine arm will receive 15 mg of plain bupivacaine HCL (the equivalent of 13.3 mg bupivacaine base) providing a 1:1 reference to the starting dose level chosen for EXPAREL®

Placebo Arm:

Subjects in the placebo arm will receive normal saline intrathecal injection.

Intrathecal Injection (in General):

Subject will be placed in the sitting position. After prepping the lumbar area, the drug will be injected in the lumbar intrathecal space via a single shot intrathecal injection at the L3 and L4 level. The subjects will be placed in supine position after completion of spinal injection.

The administration of the study drug and CSF tap will be limited to selected study team members. These members will be unblinded to the treatment arm as EXPAREL® is visibly different from bupivacaine or saline.

Test Product, Dose, Mode of Administration, and Lot Number:
Name: EXPAREL® (bupivacaine liposome injectable suspension) Active Ingredient: Bupivacaine, 13.3 mg/mL
Dosage: Single injection of EXPAREL®
Lot Number: To Be Determined
Mode of Administration: Injection into the Intrathecal space.
Reference Product, Dose, Mode of Administration, and Lot Numbers:
Name: Bupivacaine HCl
Active Ingredient: Bupivacaine
Dosage: Single injection into the Intrathecal space.
Mode of Administration: Injection into the Intrathecal space
Reference Product, Dose, Mode of Administration, and Lot Numbers:
Name: Placebo
Active Ingredient: Normal Saline (1 ml)
Dosage: Single injection into the Intrathecal space.
Mode of Administration: Injection into the Intrathecal space.

Pharmacokinetic Assessments:

Venous blood samples will be obtained from subjects in all cohorts and treatment arms and will be collected on Day 1 predose (up to 30 mins before drug administration), and 5 min (±5 min), 1(±1 hr), 3(±1 hr), 6(±1 hr), 12(±1 hr), 15(±1 hr), 20(±1 hr), 24(±1 hr), 30(±4 hr), 42(±4 hr), 96(±4 hr) and 144(±4 hr) hours from the end of study drug administration.

In addition, CSF samples will be obtained from all subjects except the no CSF tap (or no tap) group of EXPAREL® arm at the following times—
Day 1 predose (up to 5 mins prior to injection of study drug)
24 hours (±6 hours), in the absence of motor block
48 hours (±6 hours), in the absence of motor block
96 hours (±6 hours), in the absence of motor block In the presence of motor block at any of the above scheduled time points, the sampling time point will be delayed until the offset of the motor block is noted. The subsequent CSF sampling time point would then occur 24 hours later.

The subjects from the no CSF tap (or no tap) group of EXPAREL® arm, will serve as controls providing an accurate assessment of the PD effects of EXPAREL® without risk of drug removal during the CSF tap.

Start of drug administration is defined as the time of intrathecal needle insertion. End of drug administration is defined as the time of needle removal.

Pharmacokinetic Endpoints:

The following model-predicted PK endpoints will be determined:
Area under the plasma concentration-versus-time curve (AUC0-last and AUC0-∞).
Maximum plasma concentration (Cmax) and time of Cmax (Tmax).
The apparent terminal elimination half-life (t½el).
Apparent clearance (CL/F).
Apparent volume of distribution (Vd).

Pharmacodynamic Assessment:

Sensory Assessment:
Onset and segmental spread of sensory block will be evaluated by testing the sensitivity to pinprick and cold in the S1, L2, L3, L4, T10-11, T7-8, and T4 dermatomes
Onset of sensory block will be defined as the earliest time point after drug administration at which loss of sensation is noted below L2, such as S1, L3 and L4. Offset of sensory block will be defined as the earliest time point after onset of block at which recovery of sensation at L4 and S1 is noted. Duration of sensory block will be defined as the time between onset and offset of sensory block.

Motor Assessment:

To test onset and duration of motor effects, the following assessments will be performed:
Handheld dynamometer
Bromage scale
Berg balance scale (7 item)

Onset and offset of motor block will be defined using the handheld dynamometer at knee extension. Onset of motor block will be defined as the earliest time point after drug administration when a 20% or greater weakness from baseline is noted. Offset of motor block will be defined as the earliest time point after onset of motor block when less than 20% weakness from baseline is noted. Duration of motor block will be defined as the time between onset and offset of motor block.

Handheld dynamometer

The handheld dynamometer is a reliable and validated method of motor function assessment (Mentiplay 2015). A MicroFET2 handheld dynamometer (Hoggan Health Industries) will be used to test motor function. The dynamometer will be used to test hip flexion, knee extension, and ankle dorsiflexion. For hip and knee tests, the subject will be placed in sitting position with the hips and knees flexed at 90°. For the hip flexion test, the dynamometer is placed close to the knee joint, on the anterior part of the thigh. For the knee extension test, the dynamometer will be placed close to the ankle joint, on the anterior aspect of the leg. For ankle dorsiflexion test, the subject will be in the supine position with hips and knees extended, and ankles relaxed. The dynamometer will be placed over the metatarsal heads on the dorsum of the foot.

Bromage scale

Bromage scale will be used to characterize the motor block (Bromage 1965)

| Score | Intensity of motor block |
|---|---|
| I | Unable to move feet or knees |
| II | Able to move feet only |
| III | Just able to move knees |
| IV | Full flexion of knees and feet |

Berg balance scale (7 item)

The 7-item Berg balance scale will be used for this study (Chou 2006).

| Item description | |
|---|---|
| Sitting to standing | |
| Able to stand without using hand and stabilize independently | 2 |
| Able to stand using hands after several ties | 1 |
| Needs moderate or maximal assistance to stand | 0 |
| Standing unsupported with eyes closed | |
| Able to stand for 10 seconds safely | 2 |
| Able to stand for 3 seconds | 1 |
| Needs help to keep from falling | 0 |
| Reaching forward with outstretched arm while standing | |
| Can reach forward confidently >25 cm (10") | 2 |
| Can reach forward safely >5 cm (2") | 1 |
| Loses balance while trying/requires external support | 0 |
| Pick up object from floor from a standing position | |
| Able to pick up slipper safely and easily | 2 |
| no pick up but 2-5 cm(1-2") from slipper keeping balance independently | 1 |
| Unable to try/needs assistance to keep from losing balance or falling | 0 |
| Turning to look behind over left and right shoulders while standing | |
| Looks behind from both sides and weight shifts well | 2 |
| Turns sideways only but maintains balance | 1 |
| Needs assistance to keep from losing or falling | 0 |
| Standing unsupported one foot in front | |
| Able to place foot in tandem independently and hold for 30 seconds | 2 |
| Able to take small step independently and hold for 30 seconds | 1 |
| Loses balance while stepping or standing | 0 |
| Indicate which foot is in front | Left Right |
| Standing on one leg | |
| Able to lift leg independently and hold for >10 seconds | 2 |
| Able to lift leg independently and hold for = or >3 seconds | 1 |
| Unable to try/needs assistance to prevent fall | 0 |
| Indicate which foot is in front | Left Right |

Pharmacodynamic Endpoints:
Average time to onset of the sensory and motor block
Average duration of the sensory and motor block
Safety Assessment:
AEs and SAEs will be monitored and recorded from the time the ICF is signed through Day 30. All AEs and SAEs should be reported by the study staff within 24 hours of occurrence of the event.

In the event of an AE or SAE, the following safety measurements will be performed and recorded:
Sensory test (pinprick and cold test)
Motor test (handheld dynamometer, Bromage scale and Berg balance scale (7 item)), if possible
3-lead ECG
Neurological history questionnaire
Vital signs (HR, BP, cardiac output, RR, $CO_2$ and $O_2$ saturation)
Additional blood and/or CSF samples may be obtained, at the discretion of the investigator.
Phone call Day 30 (±3 days)

Neurological History Questionnaire:
Responses to the following questions will be recorded at screening, Day 1 (pre-dose-up to 3 hr prior to drug administration), at each sensory and motor assessment (Day 1-5), at discharge (Day 6), follow up visit (Day 9), Day 30 (±3 days) phone call and in the event of an AE.
Do you have any back pain? If yes, where? Describe the quality and severity. Does it radiate into your legs? If so, where?
Do you have any feeling of weakness in your legs? If so, where?
Do you have any numbness/tingling in your legs? If so, where?
Do you have any numbness/strange sensations in your buttock or perineal area?
Have you had any issues with bowel or bladder incontinence?

Safety Endpoints:
The following safety endpoints will be assessed based on the safety assessments throughout the study
Incidence of treatment-emergent AEs (TEAEs) through Day 9.
Proportion of subjects who have any of the neurological events.

LIST OF ACRONYMS/ABBREVIATIONS

| | |
|---|---|
| AE | Adverse event |
| ALT | Alanine aminotransferase |

| | |
|---|---|
| ASA | American Society of Anesthesiologists |
| AST | Aspartate aminotransferase |
| AUC | Area under the curve |
| BP | Blood pressure |
| CFR | Code of Federal Regulations |
| CL/F | Apparent clearance |
| $C_{max}$ | The maximum observed plasma concentration obtained directly from the experimental data without interpolation |
| $CO_2$ | Carbon dioxide |
| CRF | Case Report Form |
| CSF | Cerebrospinal fluid |
| DEC | Dose escalation committee |
| ECG | Electrocardiogram |
| EDTA | Ethylenediaminetetraacetic acid |
| EPRU | Early Phase Research Unit |
| FDA | Food and Drug Administration |
| FSH | Follicle stimulating hormone |
| GCP | Good Clinical Practice |
| HIV | Human immunodeficiency virus |
| HR | Heart rate |
| ICF | Informed consent form |
| ICH | International Conference on Harmonisation |
| IND | Investigational New Drug |
| IRB | Institutional Review Board |
| IV | Intravenous |
| MedDRA | Medical Dictionary for Regulatory Activities |
| NDA | New Drug Application |
| NSAIDs | Non-steroidal anti-inflammatory drugs |
| $O_2$ | Oxygen |
| PD | Pharmacodynamic |
| PICC | Peripherally inserted central catheter |
| PK | Pharmacokinetic |
| PO | Oral |
| PTAE | Pretreatment adverse event |
| RR | Respiratory rate |
| SAE | Serious adverse event |
| SAP | Statistical analysis plan |
| sNDA | Supplemental New Drug Application |
| SOC | Standard of care |
| $t_{1/2el}$ | The apparent terminal elimination half-life |
| TEAE | Treatment-emergent adverse event |
| $T_{max}$ | The time to maximum plasma concentration |
| ULN | Upper limit of normal |
| US | United States (of America) |
| Vd | Apparent volume of distribution |
| WOCBP | Women of childbearing potential |

The invention claimed is:

1. A method of treating pain in a subject, the method comprising injecting into the subarachnoid space at the L3 and L4 level of the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

2. The method of claim 1, wherein the aqueous phase further comprises hydrochloric acid.

3. The method of claim 1, wherein the amphipathic lipid is selected from the group consisting of phosphatidylcholines, phosphatidylethanolamines, sphingomyelins, lysophosphatidylcholines, lysophosphatidylethanolamines, phosphatidylglycerols, phosphatidylserines, phosphatidylinositols, phosphatidic acids, cardiolipins, diacyl dimethylammonium propanes, and stearylamines.

4. The method of claim 1, wherein the neutral lipid is at least one triglyceride.

5. The method of claim 1, wherein the pharmaceutical composition comprises a therapeutically effective amount of bupivacaine phosphate.

6. The method of claim 1, wherein the pharmaceutical composition comprises from about 10 mg to about 60 mg of bupivacaine phosphate.

7. The method of claim 6, wherein the pharmaceutical composition comprises from about 20 mg to about 60 mg of bupivacaine phosphate.

8. The method of claim 6, wherein the pharmaceutical composition comprises from about 30 mg to about 60 mg of bupivacaine phosphate.

9. The method of claim 1, wherein the method comprises administering the pharmaceutical composition by epidural injection.

10. The method of claim 1, wherein the method does not comprise administering the pharmaceutical composition by epidural injection.

11. The method of claim 1, wherein the method does not comprise administering an opioid to the subject following the injection of the pharmaceutical composition into the subarachnoid space of the subject.

12. The method of claim 1, wherein the method comprises administering an opioid to the subject following the injection of the pharmaceutical composition into the subarachnoid space of the subject.

13. The method of claim 12, wherein the opioid is oxycodone and the method comprises administering oxycodone in a total amount less than 15 mg in the first about 72 hours following the injection of the pharmaceutical composition into the subarachnoid space of the subject.

14. The method of claim 1, wherein the method comprises administering a non-opioid analgesic to the subject following the injection of the pharmaceutical composition into the subarachnoid space of the subject.

15. The method of claim 1, wherein the subject has an AUC for VAS pain intensity scores over the first 72 hours following the injection of the pharmaceutical composition into the subarachnoid space of the subject of from about 100 to about 200.

16. The method of claim 1, wherein the subject has a pruritus score as determined by the 5-D itch scale of about 10 to about 20.

17. The method of claim 1, wherein the plasma concentration of bupivacaine in the subject after about 120 hours following the injection of the pharmaceutical composition into the subarachnoid space of the subject is about is about 150 ng/mL to about 250 ng/mL.

18. The method of claim 1, wherein the pain is abdomen pain.

19. The method of claim 1, wherein the pain is pelvic pain.

* * * * *